United States Patent

Mitariten et al.

Patent Number: 5,227,567
Date of Patent: Jul. 13, 1993

[54] SEPARATION PROCESS FOR THE PRODUCT STREAMS RESULTING FROM THE DEHYDROGENATION OF HYDROCARBONS

[75] Inventors: Michael J. Mitariten, Peekskill, N.Y.; Norman H. Scott, Arlington Heights, Ill.

[73] Assignee: UOP, Des Plaines, Ill.

[21] Appl. No.: 825,886

[22] Filed: Jan. 27, 1992

[51] Int. Cl.$^5$ .............................. C07C 5/09; C07C 7/00; C07C 7/13
[52] U.S. Cl. ................................. 585/661; 585/660; 585/809; 585/829
[58] Field of Search ............... 585/654, 655, 809, 820, 585/660, 661, 829

[56] References Cited

U.S. PATENT DOCUMENTS

| | | | |
|---|---|---|---|
| 3,691,246 | 9/1972 | Parker et al. | 585/655 |
| 4,133,842 | 1/1979 | Anderson | 585/809 |
| 4,329,516 | 5/1982 | Al-Muddaris | 585/654 |
| 4,381,418 | 4/1983 | Gewartowski et al. | 585/655 |
| 4,430,517 | 2/1984 | Imai et al. | 585/660 |
| 4,469,811 | 9/1984 | Lucien | 502/227 |
| 4,486,547 | 12/1984 | Imai et al. | 502/223 |
| 5,012,037 | 4/1991 | Doshi et al. | 585/822 |

*Primary Examiner*—Anthony McFarlane
*Attorney, Agent, or Firm*—Thomas K. McBride; John G. Tolomei; John G. Cutts, Jr.

[57] ABSTRACT

A process for the separation and recovery of the product stream resulting from the dehydrogenation of dehydrogenatable hydrocarbons which process utilizes a chiller system for the recovery of olefin product liquid and a pressure swing adsorption unit to concentrate the olefin product liquid which is not recovered by the chiller.

10 Claims, 1 Drawing Sheet

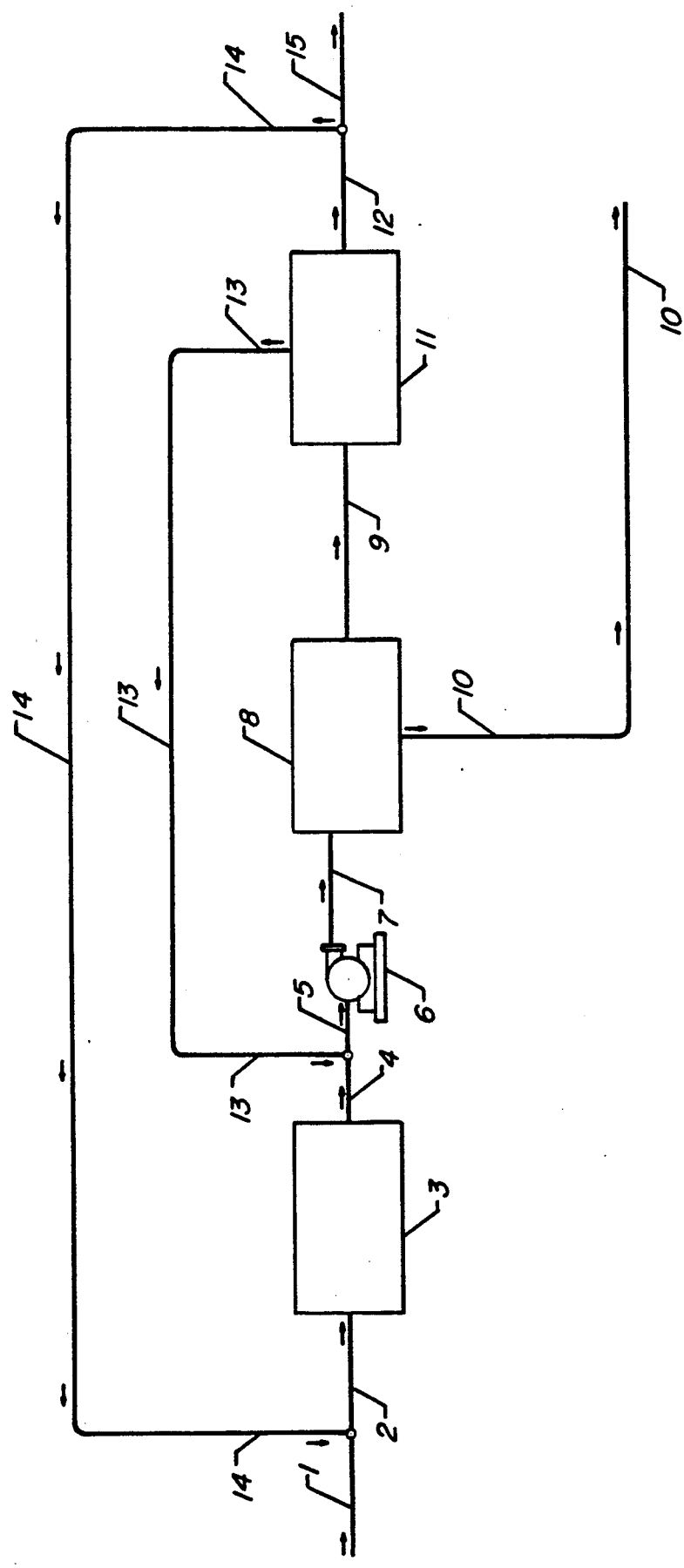

SEPARATION PROCESS FOR THE PRODUCT STREAMS RESULTING FROM THE DEHYDROGENATION OF HYDROCARBONS

FIELD OF THE INVENTION

The present invention is directed towards an improved process for the separation and recovery of the product stream resulting from the dehydrogenation of dehydrogenatable hydrocarbons. More specifically, the invention utilizes a chiller system for the recovery of olefin product liquid and a pressure swing adsorption unit to concentrate the olefin product liquid which is not recovered by the chiller.

BACKGROUND OF THE INVENTION

Dehydrogenating hydrocarbons is an important commercial hydrocarbon conversion process because of the great demand for dehydrogenated hydrocarbons for the manufacture of various chemical products such as detergents, high octane motor fuels, pharmaceutical products, plastics, synthetic rubbers, polymerization monomers and other products well known to those skilled in the art. Processes for the dehydrogenation of light acyclic hydrocarbons are well known to those skilled in the hydrocarbon conversion arts. For instance, the dehydrogenation of $C_2$–$C_5$ paraffins is well known. Because the light paraffins are relatively volatile, a more complicated separation scheme and a bulk condensation is normally required to effect the separation of the product olefins from the light by-products and hydrogen which are simultaneously produced in the process. It is therefore believed that U.S. Pat. No. 4,381,418 (Gewartowski et al) is pertinent for its teaching of a catalytic dehydrogenation process for $C_2+$ normally gaseous paraffinic hydrocarbons and the recovery of the products of the reaction. U.S. Pat. Nos. 4,430,517 and 4,486,547 issued to Imai et al and U.S. Pat. No. 4,469,811 issued to Lucien are believed pertinent for their teaching of catalysts and operating conditions which can be employed for the dehydrogenation of low molecular weight paraffins.

Pressure swing adsorption (PSA) provides an efficient and economical means for separating a multi-component gas stream containing at least two gases having different adsorption characteristics. The more-strongly adsorbable gas can be an impurity which is removed from the less-strongly adsorbable gas which is taken off as product; or, the more-strongly adsorbable gas can be the desired product, which is separated from the less-strongly adsorbable gas. For example, it may be desirable to remove carbon monoxide and light hydrocarbons from a hydrogen-containing feed stream to produce a purified (99+%) hydrogen stream for a hydrocracking or other catalytic process where these impurities could adversely affect the catalyst or the reaction. On the other hand, it may be desirable to recover more-strongly adsorbable gases, such as ethylene, from a feed to produce an ethylene-rich product.

In pressure swing adsorption, a multi-component gas is typically fed to at least one of a plurality of adsorption beds at an elevated pressure effective to adsorb at least one component, while at least one other component substantially passes through. At a defined time, feed to the adsorber is terminated and the bed is depressurized by one or more co-current to the direction of feed depressurization steps wherein pressure is reduced to a level which permits the separated, less-strongly adsorbed component or components remaining in the bed to be drawn off without significant removal of the more strongly adsorbed components. Then, the bed is depressurized by a countercurrent depressurization step wherein the pressure on the bed is further reduced by withdrawing desorbed gas countercurrently to the direction of feed. Finally, the bed is purged and repressurized.

Those skilled in the art of hydrocarbon processing, more particularly the dehydrogenation of hydrocarbons, are constantly searching for ways to recover a liquid product from a dehydrogenation zone in the most convenient and economical manner.

BRIEF SUMMARY OF THE INVENTION

The invention provides a process for the production of olefinic hydrocarbons at essentially 100% recovery as well as an enriched hydrogen product without requiring severe cryogenic processing conditions. This integrated process achieves the demonstrated advantages by the use of a chiller system for the recovery of the paraffin/olefin product and a pressure swing adsorption unit (PSA) to concentrate the hydrocarbon compounds and recycle the olefin and unconverted paraffins which are unrecovered by the chiller. This integration allows for the recovery of up to 100% of the produced olefin as liquid product and the production of an enriched hydrogen stream essentially free of paraffin and olefin.

One broad embodiment of the present invention may be characterized as a process for the dehydrogenation of a dehydrogenatable hydrocarbon which process comprises: (a) contacting the dehydrogenatable hydrocarbon with a dehydrogenation catalyst in a dehydrogenation zone at dehydrogenation conditions to produce a hydrocarbon effluent stream comprising dehydrogenated hydrocarbons, unconverted dehydrogenatable hydrocarbons and hydrogen; (b) compressing the hydrocarbon effluent stream comprising dehydrogenated hydrocarbons, unconverted dehydrogenatable hydrocarbons and hydrogen to produce a compressed stream; (c) cooling the compressed stream to a temperature less than about 100° F. (38° C.); (d) introducing the resulting compressed, cooled stream produced in step (c) into a vapor-liquid separator: (e) withdrawing from the vapor-liquid separator a liquid stream comprising at least a majority of the dehydrogenated hydrocarbons and the unconverted dehydrogenatable hydrocarbon contained in the hydrocarbon effluent stream; (f) withdrawing from the vapor-liquid separator a hydrogen-rich gaseous stream comprising a minority of the of dehydrogenated hydrocarbons and unconverted dehydrogenatable hydrocarbons; (g) passing the hydrogen-rich gaseous stream from step (f) to an adsorber bed containing adsorbent having adsorptive capacity for hydrocarbons at effective adsorption conditions; and (h) withdrawing a hydrogen-rich gaseous stream having a reduced concentration of hydrocarbons from said adsorber bed.

Other embodiments of the subject invention encompass further details such as preferred feedstocks, dehydrogenation catalysts, adsorbents and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

Olefinic hydrocarbons are one of the major building blocks of a large number of petrochemical products. Olefinic hydrocarbons are also useful in petroleum refineries for the production of motor fuel blending components. The process of the present invention possesses utility in providing facile production of these olefinic hydrocarbons. Based upon the commercial desirability to produce olefinic hydrocarbons, there is a constant search for techniques to lower the cost of production of these olefins. We have discovered an integrated dehydrogenation products separation process with enhanced economics and the details of which process are herein described.

The term "dehydrogenatable hydrocarbons" as utilized herein is meant to refer to all classes of hydrocarbons containing saturated carbon bonds which have the potential for forming one or more unsaturated bonds through the process of dehydrogenation. The preferred dehydrogenatable hydrocarbons of the present invention consist of paraffinic type hydrocarbons. More specifically, the paraffin hydrocarbon charge stock of the present invention may contain from 2 carbon atoms to about 30 carbon atoms. Representative members of this class are: ethane, propane, butane, pentane, hexane, heptane, nonane, decane, undecane, dodecane, tridecane, tetradecane, pentadecane, hexadecane, heptadecane, octadecane, and mixtures thereof. A particularly important class of charge stocks include ethane, propane, butane, pentane and mixtures thereof and which are readily prepared by the fractionation of relatively low boiling point hydrocarbon fractions. Another important charge stock contains normal paraffins of about 10 to about 15 carbon atoms since these produce a mono-olefin which can be utilized to make detergents having superior biodegradability and detergency. For example, a mixture containing a 4 or 5 homolog spread, such as $C_{11}$ to $C_{14}$, $C_{10}$ to $C_{13}$, $C_{11}$ to $C_{15}$, provides an excellent charge stock. Moreover, it is preferred that the amount of nonnormal hydrocarbons present in this normal paraffin stream be kept at low levels. Thus, it is preferred that this stream contain greater than 90 wt. % normal paraffin hydrocarbons, with best results achieved at purities in the range of 96–99 wt. % or more. Although various types of hydrocarbon feedstocks may be utilized in the process of the present invention, for purposes of specific exemplification, a feed stream comprising propane is described in detail.

The selected dehydrogenatable hydrocarbon feedstock is introduced into a dehydrogenation zone containing dehydrogenation catalyst and operated at dehydrogenation conditions to convert at least a portion of the dehydrogenatable hydrocarbons to produce a hydrocarbon stream comprising dehydrogenated hydrocarbons and unconverted dehydrogenatable hydrocarbons. Preferably, the unconverted dehydrogenatable hydrocarbons are separated and recycled to the dehydrogenation zone together with the fresh feedstock.

The dehydrogenation catalyst may be employed in a fixed bed, fluidized bed, or a moving bed. Moreover, the dehydrogenation catalytic reaction zone may consist of multiple catalyst beds. In one such system, the catalyst is employed within an annular bed through which it is movable via gravity flow. In such a system, it is common practice to remove catalyst from the bottom of the reaction zone, regenerate it and then return it to the top of the reaction zone. Any suitable dehydrogenation catalyst may be used in the process of the present invention. Generally, the preferred catalyst comprises a platinum group metal component, an alkali metal component and a porous inorganic carrier material. The catalyst may also contain promoter metals which advantageously improve the performance of the catalyst. It is preferably that the porous carrier material of the dehydrogenation catalyst be an absorptive high surface area support having a surface area of about 25 to about 500 $m^2/g$. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxides, magnesia, silica alumina, alumina boria; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16".

The preferred dehydrogenation catalyst also contains a platinum group metal component. Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.2 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 3.5 wt. %, but is preferably between 0.2 and about 2.5 wt. % calculated on an elemental basis. This component may be added to the catalyst by the methods described above as a separate step or simultaneously with the solution of another component.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The dehydrogenation conditions which will be employed in the process of the present invention will of course vary depending on such factors as catalyst activity, feedstock, and desired conversion. A general range of conditions which may be employed for dehydrogenation of a light hydrocarbon include a temperature of from about 1022° F. (550° C.) to about 1472° F. (800° C.) a pressure of from about 0.01 to about 10 atmospheres absolute, a liquid hourly space velocity between about 0.1 and about 100 hr$^{-1}$ and a hydrogen to hydrocarbon mole ratio from about 0.01:1 to about 40:1.

In accordance with the present invention, a hydrocarbon stream, for example, comprising propylene, propane, ethylene, ethane, methane, hydrogen and, in some cases, carbon dioxide, carbon monoxide and water is removed from the dehydrogenation reaction zone and is compressed to a pressure in the range from about 70 psig (482 kPa gauge) to about 1000 psig (6895 kPa gauge). The resulting compressed hydrocarbon stream is cooled to a temperature in the range from about −20° F. (−29° C.) to about 100° F. (38° C.) and introduced into a vapor-liquid separator. A liquid stream comprising at least a majority of the dehydrogenated hydrocarbons and the unconverted dehydrogenatable hydrocarbons contained in the effluent from the dehydrogenation zone is withdrawn from the vapor-liquid separator and recovered. A hydrogen-rich gaseous stream comprising a minority of the dehydrogenated hydrocarbons and unconverted dehydrogenatable hydrocarbons is removed from the vapor-liquid separator and is passed to an adsorber bed containing adsorbent having adsorptive capacity for hydrocarbons at effective adsorption conditions. An effluent from the adsorber bed comprising a hydrogen-rich gaseous stream and having a reduced concentration of hydrocarbons is recovered. At least a portion of the hydrogen-rich gaseous stream may be recycled to the dehydrogenation reaction zone, used to regenerate a spent adsorber bed, or used in some other useful manner.

Preferably the adsorber bed is a part of an integrated pressure swing adsorption (PSA) process whereby a continuous adsorber operation can be obtained while simultaneously regenerating a spent adsorber bed.

In accordance with the present invention, the pressure swing adsorption provides an efficient and economical means for separating a hydrogen-rich stream from trace quantities of hydrocarbons. We contemplate that the PSA part of the present invention comprises a plurality of adsorption zones maintained at an elevated pressure effective to adsorb hydrocarbons while letting the hydrogen pass through the adsorber bed. At a defined time, the passing of the adsorber feed to one adsorber bed is discontinued and the adsorber bed is depressured by one or more co-current depressurization steps wherein the pressure is reduced to a defined level which permits additional hydrogen and light hydrocarbon components remaining in the adsorber bed to be withdrawn and utilized. Then the adsorber bed is depressured by a countercurrent depressurization step wherein the pressure in the adsorber bed is further reduced by withdrawing desorbed hydrocarbons countercurrently to the direction of the feed. Finally, the adsorber bed is purged and repressured. A suitable purge gas is the co-current depressurization hydrogen-rich gas produced from another adsorber vessel. The final stage of repressurization is with feed gas or light gases produced during the adsorption step.

The present invention can be performed using virtually any adsorbent material in the adsorber beds that have a preferential capacity for hydrocarbons as compared to hydrogen. Suitable adsorbents known in the art and commercially available include crystalline molecular sieves, activated carbons, activated clays, silica gels, activated aluminas and the like.

It is often desirable when using crystalline molecular sieves that the molecular sieve be agglomerated with a binder in order to ensure that the adsorbent will have suitable physical properties. Although there are a variety of synthetic and naturally-occurring binder materials available such as metal oxides, clays, silicas, aluminas, silica-aluminas, silica-zirconias, silica-thorias, silica-berylias, silica-titanias, silica-alumina-thorias, silica-alumina-zirconias, mixtures thereof and the like. Clay-type binders are preferred and examples which may be employed to agglomerate the molecular sieve without substantially altering the adsorptive properties of the zeolite are attapulgite, kaolin, volclay, sepiolite, polygorskite, kaolinite, bentonite, montmorillonite, illite and chlorite. The choice of a suitable binder and methods employed to agglomerate the molecular sieves are generally known to those skilled in the art and need not be further described herein.

The PSA cycle used in the present invention preferably includes the steps of adsorption, at least one co-current depressurization step, countercurrent desorption, purge and repressurization. Thus cycle steps are typically described with reference to their direction relative to the adsorption step. The cycle steps wherein the gas flow is in a concurrent direction to the adsorption step are known as "co-current" steps. Similarly, cycle steps wherein the gas flow is countercurrent to the adsorption step are known as "countercurrent" steps. During the adsorption step the feed stream is passed to the adsorber bed at an elevated adsorption pressure in order to cause the adsorption of the hydrocarbons and produce a hydrogen-rich gaseous stream. During the co-current depressurization steps the pressure in the depressurizing bed is released and the effluent obtained therefrom, which is rich in hydrogen, is passed in a countercurrent direction to another adsorber bed undergoing purge or repressurization. Typically, more than one co-current depressurization step is used wherein a first equalization step is performed after which a provide purge step is initiated wherein the adsorber bed is further co-currently depressured to provide a purge gas that is relatively impure with respect to the adsorbed component and thus is suitable for use as a purge gas. Optionally, a portion of hydrogen-rich adsorption effluent gas having a reduced concentration of hydrocarbons or an externally supplied gas can be used to supply the purge gas. Upon the completion of the co-current depressurization step, if employed, the adsorber bed is countercurrently depressurized to a desorption pressure in order to desorb the hydrocarbons. Upon completion of the desorption step, the adsorber bed is purged countercurrently with purge gas typically obtained from another bed. Finally, the adsorber bed is repressurized, first, typically with equalization gas from other adsorber beds and then with feed or product gas to adsorption pressure. Other additional steps known to those skilled in the art, such as, for example, a co-purge step wherein the adsorber bed is co-currently purged of the less strongly adsorbed components at an elevated pressure such as the adsorption pressure with a purge stream comprising hydrocarbons, can be employed.

The adsorber bed may suitably be operated at a pressure in the range from about 60 psig (413 kPa gauge) to about 1000 psig (6893 kPa gauge). The operating temperature for the adsorber bed may be selected from the range from about −20° F. (−29° C.) to about 150° F. (65.5° C.). Additional operating conditions of the adsorber bed such as cycle times and rates of depressurization, for example, are not critical to the present invention and may readily be selected by a person skilled in the art.

DETAILED DESCRIPTION OF THE DRAWING

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such miscellaneous equipment is well within the purview of one skilled in the art.

With reference now to the drawing, a dehydrogenatable hydrocarbon feed stream comprising propane and trace quantities of butane is introduced via conduit 1 and is admixed with a hereinafter described hydrogen-rich gaseous stream which is carried via conduit 14 and the resulting admixture is introduced via conduit 2 into dehydrogenation zone 3 to dehydrogenate at least a portion of the propane stream to provide dehydrogenated hydrocarbons. A hydrocarbon stream comprising dehydrogenated hydrocarbons and unconverted dehydrogenatable hydrocarbons is removed from dehydrogenation zone 3 via conduit 4 and is admixed with a hereinafter described recycle stream containing dehydrogenated and/or dehydrogenatable hydrocarbons provided via conduit 13 and the resulting admixture is introduced via conduit 5 into compressor 6. The compressed effluent from compressor 6 is transported via conduit 7 and is introduced into chiller 8. A resulting liquid hydrocarbon product stream containing dehydrogenated hydrocarbons and dehydrogenatable hydrocarbons is removed from chiller 8 via conduit 10. A gaseous stream comprising hydrogen and hydrocarbons is removed from chiller 8 via conduit 9 and introduced into adsorption zone 11. A hydrogen-rich gaseous stream is removed from adsorption zone 11 via conduit 12 and at least a portion is recycled via conduit 14 as hereinabove described. A net hydrogen-rich gaseous stream is removed from the process and recovered via conduit 15. A gaseous recycle stream comprising hydrocarbons and hydrogen is removed from adsorption zone 11 via conduit 13 and recycled as hereinabove described to compressor 6.

The following illustrative embodiment is presented for the purpose of further demonstrating the process of the present invention and to indicate the benefits afforded without undue limitation by the utilization thereof in maximizing the recovery of dehydrogenated hydrocarbons in an economical manner. The following data were not obtained by the actual performance of the present invention, but are considered prospective and reasonably illustrative of the expected performance of the invention.

ILLUSTRATIVE EMBODIMENT

A feed stream having a flow rate in an amount $10 \times 10^6$ standard cubic feet per day (10 MM SCFD), and having a composition of 50 volume percent hydrogen and 50 volume percent 1-butene is selected to demonstrate the process of the present invention. Although a simplified composition for the feed stream is used as the model, it is understood that the feed stream may contain other components having both higher and lower boiling points as compared to 1-butene.

The feed stream, as described hereinabove, is representative of an effluent from a catalytic dehydrogenation zone which is operated at close to atmospheric pressure. This stream is compressed to a pressure of 140 psig (965 kPa gauge) and cooled to a temperature of about 100° F. (38° C.) which causes the condensation of a portion of the 1-butene. A recycle stream which is generated during the regeneration of a spent adsorbent zone, as hereinafter described, in an amount of $3.5 \times 10^6$ standard cubic feet per day (3.5 MM SCFD) and containing 60.3 volume percent hydrogen and 39.7 volume percent butene is admixed with the compressed catalytic hydrogenation zone effluent. The resulting admixture is cooled further in a chiller to 40° F. (4.4° C.) which causes further condensation of 1-butene. A liquid 1-butene stream is produced from the effluent from the chiller in an amount equal to about 5 MM SCF and containing 99.4 volume percent 1-butene and 0.6 volume percent hydrogen.

A gas stream effluent from the chiller is produced in an amount of 8.5 MM SCF at 120 psig (827 kPa gauge) and containing 83.5 volume percent hydrogen and 16.5 volume percent 1-butene. The effluent gas stream from the chiller is introduced into an adsorber bed containing an adsorbent which selectively adsorbs 1-butene at conditions which include a pressure of about 120 psig (827 kPa gauge) and a temperature of about 40° F. (4.4° C.). A high purity hydrogen-rich gaseous stream is then recovered from the adsorber bed and containing 99.999+ volume percent hydrogen while containing only 10 ppm 1-butene. A portion of the hydrogen contained in the feed is used to regenerate a spent adsorber bed to remove adsorbed 1-butene thereby producing a recycle stream in an amount of 3.5 MM SCF and containing 60.3 volume percent hydrogen and 39.7 volume percent 1-butene which is admixed with the effluent from the dehydrogenation zone as described hereinabove.

The foregoing description, drawing and illustrative embodiment clearly illustrate the advantages encompassed by the method of the present invention and the benefits to be afforded with the use thereof.

What is claimed:

1. A process for the dehydrogenation of a dehydrogenatable hydrocarbon which process comprises:
   (a) contacting said dehydrogenatable hydrocarbon with a dehydrogenation catalyst in a dehydrogenation zone at dehydrogenation conditions to produce a hydrocarbon effluent stream comprising dehydrogenated hydrocarbons, unconverted dehydrogenatable hydrocarbons and hydrogen;
   (b) compressing said hydrocarbon effluent stream comprising dehydrogenated hydrocarbons, unconverted dehydrogenatable hydrocarbons and hydrogen to produce a compressed stream;
   (c) cooling said compressed stream to a temperature in the range from about −20° F. (29° C.) to about 100° F. (38° C.);
   (d) introducing the resulting compressed, cooled stream produced in step (c) into a vapor-liquid separator:
   (e) withdrawing from said vapor-liquid separator a liquid stream comprising at least a majority of said dehydrogenated hydrocarbons and said unconverted dehydrogenatable hydrocarbon contained in said hydrocarbon effluent stream;
   (f) withdrawing from said vapor-liquid separator a hydrogen-rich gaseous stream comprising a minority of said dehydrogenated hydrocarbons and unconverted dehydrogenatable hydrocarbons;
   (g) passing said hydrogen-rich gaseous stream from step (f) to an adsorber bed containing adsorbent having adsorptive capacity for hydrocarbons at effective adsorption conditions;
   (h) withdrawing a hydrogen-rich gaseous stream having a reduced concentration of hydrocarbons from said adsorber bed; and
   (i) recycling at least a portion of said hydrogen-rich gaseous stream having a reduced concentration of hydrocarbons from step (h) to said dehydrogenation zone.

2. The process of claim 1 wherein said liquid stream comprising at least a majority of said dehydrogenated hydrocarbons and said unconverted dehydrogenatable hydrocarbons produced in step (e) is separated to produce a dehydrogenated hydrocarbon product stream and an unconverted dehydrogenatable hydrocarbon stream.

3. The process of claim 2 wherein said unconverted dehydrogenatable hydrocarbon stream is recycled.

4. The process of claim 1 wherein said dehydrogenatable hydrocarbon feedstock is selected from the group consisting of ethane, propane, butane and pentane.

5. The process of claim 1 wherein said dehydrogenation conditions include a temperature from about 1022° F. (550° C.) to about 1472° F. (800° C.), a pressure from about 0.01 to about 10 atmospheres absolute, a liquid hourly space velocity from about 0.1 to about 100 hr$^{-1}$ and a hydrogen to hydrocarbon mole ratio from about 0.01:1 to about 40:1.

6. The process of claim 1 wherein said dehydrogenatable catalyst comprises a platinum group metal component, an alkali metal component and a porous inorganic carrier material.

7. The process of claim 1 wherein said adsorber bed containing adsorbent is regenerated by passing at least a portion of said hydrogen-rich gaseous stream produced in step (h) to desorb hydrocarbons thereby regenerating said adsorbent.

8. The process of claim 7 wherein an effluent stream comprising hydrogen and desorbed hydrocarbons from said adsorber bed is compressed in step (b) in order to recover said desorbed hydrocarbons.

9. The process of claim 1 wherein said adsorber bed containing adsorbent is regenerated by passing at least a portion of a co-current depressurization hydrogen-rich gaseous stream to desorb hydrocarbons thereby regenerating said adsorbent.

10. The process of claim 9 wherein an effluent stream comprising hydrogen and desorbed hydrocarbons from said adsorber bed is compressed in step (b) in order to recover said desorbed hydrocarbons.

* * * * *